US007915016B2

(12) United States Patent
Liss

(10) Patent No.: US 7,915,016 B2
(45) Date of Patent: Mar. 29, 2011

(54) CDNA PRODUCTION FROM CELLS AFTER LASER MICRODISSECTION

(75) Inventor: Birgit Liss, Marburg (DE)

(73) Assignee: Philipps-Universitat Marburg, Marburg (DE)

( * ) Notice: Subject to any disclaimer, the term of this patent is extended or adjusted under 35 U.S.C. 154(b) by 443 days.

(21) Appl. No.: 11/569,741

(22) PCT Filed: May 27, 2005

(86) PCT No.: PCT/DE2005/000979

§ 371 (c)(1), (2), (4) Date: Jun. 24, 2008

(87) PCT Pub. No.: WO2005/116245

PCT Pub. Date: Dec. 8, 2005

(65) Prior Publication Data

US 2008/0261275 A1 Oct. 23, 2008

(30) Foreign Application Priority Data

May 28, 2004 (DE) ........................ 10 2004 026 744

(51) Int. Cl.
*C12P 19/34* (2006.01)
*C07H 21/04* (2006.01)
*C12N 9/00* (2006.01)

(52) U.S. Cl. .................. 435/91.51; 435/183; 536/24.33

(58) Field of Classification Search ........................ None
See application file for complete search history.

(56) References Cited

U.S. PATENT DOCUMENTS

| | | | | |
|---|---|---|---|---|
| 5,998,129 | A | 12/1999 | Schuetze et al. | 435/4 |
| 6,096,507 | A * | 8/2000 | Weinshank et al. | 435/7.21 |
| 2002/0127638 | A1 * | 9/2002 | Flor et al. | 435/69.1 |
| 2002/0156035 | A1 * | 10/2002 | Reinhard et al. | 514/44 |
| 2002/0198361 | A1 * | 12/2002 | Rougeot et al. | 530/350 |
| 2003/0166190 | A1 * | 9/2003 | Wright et al. | 435/183 |
| 2004/0022727 | A1 * | 2/2004 | Stanton et al. | 424/1.49 |
| 2004/0253661 | A1 * | 12/2004 | Goldrick et al. | 435/40.5 |

OTHER PUBLICATIONS

Tietjen et al., "Single-cell transcriptional analysis of neuronal progenitors," Neuron, 2003, vol. 38, No. 2, pp. 161-175.*

Schultz et al. "RNasin® Ribonuclease Inhibitor Part II: A Tale of Two Proteins" [online, retrieved on May 25, 2009], retrieved from http://www.promega.com/pnotes/77/9028_12/9028_12.pdf.*

Shirakawa et al. Hemodynamics in Vasculogenic Mimicry and Angiogenesis of Inflammatory Breast Cancer Xenograft. Cancer Research 62:560-566, Jan. 15, 2002.*

Glasgow et al. Single cell reverse transcription-polymerase chain reaction analysis of rat supraoptic magnocellular neurons: neuropeptide phenotypes and high voltage-gated calcium channel subtypes. Endocrinology 140:5391-5401 (1999).*

Winslow et al. Polyinosinic acid as a carrier in the microscale purification of total RNA. Nucleic Acids Research 19(12):3251-3 (1991).*

Tietjen Ian et al: "Single-cell transcriptional analysis of neuronal progenitors." Neuron. Apr. 2003, vol. 38, No. 2, pp. 161-175.

Kamme Frederik et al: "Single-cell microarray analysis in hippocampus CA1: demonstration and validation of cellular heterogenity." The Journal of Neuroscience, May 2003, vol. 23 No. 9, p. 3608.

Busche S et al: "Expression of angiotensin AT(1) and AT(2) receptors in adult reat cardiomyocytes after mycardial infarction. A single-cell reverse transcriptase-polymerase chain reaction study." American Journal of Pathology, Aug. 2000, vol. 157, No. 2, pp. 605-611.

Hahn Sinuhe et al: "Single cell PCR in laser capture microscopy", Methods in Enzymology. 2002, vol. 356, 2002, pp. 295-301.

Todd Randy et al: "Challenges of cingle-cell diagnostics: analysis of gene expression." Trends in Molecular Medicine. Jun. 2002, vol. 8, No. 6, pp. 254-257.

* cited by examiner

*Primary Examiner* — Samuel C Woolwine

(74) *Attorney, Agent, or Firm* — Jonathan Myers; Andrew Wilford

(57) ABSTRACT

The present invention provides a new procedure for the synthesis of cDNA from single cells after microdissection. It has the advantage that it is cost-efficient and can be carried out quickly with only few steps, even by less skilled laboratory employees. For the first time, the time-consuming and risky step of RNA isolation is omitted during cDNA synthesis from single cells by performing lysis and cDNA synthesis in the same reaction tube and in one buffer solution, which provides reliable and contamination-free results. The buffer is composed of NP40, carrier-RNA and Super RNAsin, as well as dNTPs and cDNA synthesis primers.

13 Claims, No Drawings

CDNA PRODUCTION FROM CELLS AFTER LASER MICRODISSECTION

CROSS REFERENCE TO RELATED APPLICATIONS

This application is the US national Phase of PCT/DE2005/000979 filed 27 May 2005, and claims the benefit of the priority of German Patent Application No. 102004026744.8 filed 28 May 2004, both of which are incorporated by reference herein. The International Application was published in German on 8 Dec. 2005 as WO 2005/116245 A2.

The present invention concerns a procedure for the contamination-free isolation of single cells from fixed tissue by laser microdissection, followed by an analytical and preparative investigation thereof, particularly with regard to the cDNA-synthesis of single neurons from fixed brain slices with single-cell sensitivity.

DESCRIPTION AND INTRODUCTION INTO THE GENERAL FIELD OF INVENTION

Microdissection is a procedure used in biosciences which allows the separation of isolated or tissue-localized cellular, supra-cellular and subcellular structures, which thus are rendered available for further analytical and preparative procedures.

Among the microdissection techniques, the Laser Capture Microdissection-technique (also referred to as LCM) plays a specific role. The microdissection is performed manually or in motorized fashion by micromanipulation in direct contact with the sample or contact-free using focused lasers.

The U.S. Pat. No. 5,998,129 describes a laser microdissection technique where a desired section of a tissue sample which is attached to a planar object slide, e.g. cell organelles or a single cell, is cut out of the surrounding tissue by laser beam. The isolated cell remaining on the object slide is mobilized with an additional laser pulse into the direction of the laser beam and collected in a reaction vial.

One of the further analytical and preparative procedures for cells which were isolated by laser microdissection is the isolation of nucleic acids, DNA, RNA, in particular mRNA. At present, commercial kits are available, e.g. from the companies PALM (PALM RNA\Extraction Kit) and Qiagen (Qiagen RNAeasy Micro Kit), which allow the isolation of mRNA from laser-microdissected cells. However, mRNA isolations performed with these kits provide no acceptable, reproducible results for isolated single cells.

Kamme Feta I (2003) J Neurosci 23(9), and Tietjen I et al (2003) Neuron 38 used the laser microdissection instrument of the company Arcturus and describe a procedure which is indeed less complicated than commercial kits with respect to application and yield but allows no contamination-free collection of single specific cells. Particularly with regard to the preparation of single neurons from fixed brain slices (e.g. post-mortem human), a contamination with neighboring glia cells is problematic. At present, no procedure is known which allows the extraction of good-quality mRNA from single cells after contact-free laser microdissection with the PALM system.

The aim of the present invention is to eliminate the disadvantages of the state-of-the-art technique as described above and to provide a simple and fast procedure for the direct cDNA-synthesis from isolated cells of a tissue sample after laser microdissection.

This problem is solved by the present invention by a procedure for a combined lysis and direct cDNA synthesis according to the claims.

The procedure includes the following steps:

1. Preparation of cells after laser microdissection and transfer into reaction tubes
2. Lysis of cells according to step 1 and reverse transcription of RNA from these cells according to step 1 in a lysis/cDNA-synthesis reaction buffer and in a reaction vial The procedure according to the present invention has the advantage of being cost-efficient and can be carried out quickly with only few steps even by less skilled laboratory employees. Important is that the time-consuming and risky step of RNA isolation is omitted and replaced by a combined lysis and direct cDNA synthesis in the same reaction tube, which provides reliable, contamination-free results. For the detection of cDNA, a direct PCR can be carried out in the same reaction vial without any further purification or other additional steps. The composition of the buffer (i.e. NP40, Poly-I Carrier and Super RNAsin, as well as dNTPs and cDNA synthesis primers) which is used as lysis/cDNA-synthesis reaction buffer is adjusted particularly for this purpose. Further steps such as sample preparation and staining, conduction of the incubation protocol, and compliance with default temperatures optimize the RNA/cDNA-yield.

As cells, intact cells from a suspension or culture or fixed, dehydrated slice preparations are used. By using a drying agent e.g. silica and the addition of a molecular sieve to the alcohol it is guaranteed that the tissue sample is dry enough for laser dissection in a very short time. Simultaneously, the complete dehydration minimizes the loss of template due to RNAse activity.

Lysis and cDNA synthesis are preferably performed directly in the same reaction vial, even in the same reaction buffer (lysis/cDNA-synthesis reaction buffer). A separate RNA isolation is not required. Alternatively, prior to cDNA synthesis a DNAse digest is carried out. The lysis/cDNA-synthesis reaction buffer according to the present invention has no influence on a subsequent direct qualitative PCR amplification, so that this reaction is also performed in the same reaction vial. For carrying out a quantitative real-time PCR analysis, a additional purification step is introduced alternatively, since it is well known that components of the cDNA reaction mix disturb the kinetics of a PCR amplification. Such purification steps are well known to the experts in this field, and the state-of-the art can be looked up e.g. in Liss, Nuc Acids Research, 2002.

EMBODIMENTS

1. Preparation of Cells after Laser Microdissection and Transfer into Reaction Vials The preparation of single fixed cells or a single fixed cell after laser microdissection includes the preparation of a suitable tissue sample. The tissue sample originates from organs and tissues of vertebrates, i.e. animals and human beings, which were obtained by conventional procedures such as biopsy or taxidermy, for instance a tissue sample is a brain sample of a vertebrate obtained by taxidermy and cryostat-cutting. For this purpose the brain of a vertebrate e.g. a mouse is taken out under sterile conditions on ice, and frontal cortex and caudal cerebellum are removed. The mid brain is placed on an microscope slide and embedding medium is added (e.g. tissue freezing medium of the company Jung), followed by freezing at −20° C. on a snap-freezing device (−45° C.). After approx. 20 min, sections with a thickness of 12 μm are obtained at a cryostat temperature of −19° C. These sections are subsequently placed on a sterile object slide (e.g. PALM, PEN 1 mm glass). Fixing and staining of the tissue specimen is performed e.g. by staining the sections with cresyl violet (e.g. Cresyl Violet acetate Staining Dye of Sigma, C 5042). Alternatively to conventional cresyl violet staining procedures, a very fast staining in a 100% cresyl violet solution in alcohol is preferred. The staining procedure is followed by a, however shortened, procedure with increasing ethanol steps which is well known to those skilled in the art, whereupon the sections are incubated according to the following protocol:

| | |
|---|---|
| 1. 75% ethanol (−20° C. pre-cooled) | duration: 2 min |
| 2. cresyl violet, a few drops using a sterile syringe with filter | duration: 30 sec |
| 3. 75% ethanol | duration: 1-5 sec |
| 4. 100% ethanol | duration: 1-5 sec |
| 5. 100% ethanol on a molecular sieve | duration: 1 min |

Alternatively, also other staining procedures are performed which are well known to those skilled in the art. In order to obtain a preferably complete dehydration of the tissue specimen it is advantageous to use a molecular sieve, for example the molecular sieve of the company VWR Merck Perlform 0.3 nm and 2 mm, ordering number 1.057.041.000, in 100% ethanol.

After the final alcohol step, the slices are dried in a box with drying agents, e.g. silica gel. The box with silica gel (Silica Gel with moisture indicator; Merck, 1 kg Ordering No. 1.01925.1000) and the 100% ethanol reaction vial is sealed with paraffin for prolonged storage.

The laser microdissection of a single or single cells from a tissue section is performed with sterile equipment according to the manufacturer's instructions, e.g. PALM. Therefore, the laser and all instruments, e.g. pipettes, centrifuge, vortex, table are cleaned with first RNase Zap, then with RNase-free water. Single cells are cut out of e.g. the substantia nigra of the prepared tissue sample, e.g. the dehydrated brain slice, and are, depending on the sample, e.g. at a distance of 2 mm and a laser energy of 78% automatically catapulted into a vial or lid (e.g. adhesive cap when using the equipment of the company PALM). The latter has the advantage that no buffer has to be applied beforehand. Alternatively, the sterile lysis/cDNA-synthesis reaction buffer can also be provided in a conventional lid prior to the catapulting step.

2. Lysis of Cells According to Step 1 and Reverse Transcription of RNA from Cells According to Step 1 in a Lysis/cDNA-Synthesis Reaction Buffer and in a Reaction Tube After laser microdissection, 4.5 μl lysis/cDNA-synthesis reaction buffer is added to the cells in the vial or lid of the cap, respectively. Preferably, a buffer is used which has freshly been prepared under sterile and RNAse-free conditions with the following composition:

| Lysis/cDNA-synthesis reaction buffer 1x | Amount | Final conc. |
|---|---|---|
| 5x first strand buffer (Invitrogen) | 1.00 μl | 1x |
| 10x RT-buffer (see below) | 0.50 μl | 1x |
| DTT (Invitrogen; 0.1M) | 0.50 μl | 10 mM |
| Poly-I Carrier RNA (Sigma) 1 μg/mg | 0.50 μl | 500 ng |
| Super-RNAsin (20 u/μl Ambion) | 0.50 μl | 10 u |
| Nonidet P40 (1:10 dilution; RNase-free, Roche Diagnostics) | 0.25 μl | 0.5% |
| $H_2O$ | 1.25 μl | |

-continued

| 10x RT-buffer | Conc. | Final conc. |
|---|---|---|
| dNTPs (20 mM each, Amersham Pharmacia Biotech) | 5 mM | 0.5 mM |
| random hexamer primer (1 mM, Roche Diagnostics) | 50 μM | 5 μM |
| Tris HCl pH 8, 100 mM | 10 mM | 1 mM |

As cDNA-synthesis primer, for example random hexamer primer are used. As RNA-carrier, for example the Poly-I Carrier RNA is used. Further alternatives to these substances which are applied with the same effect are known to those skilled in the art.

Onto the lid, e.g. a PCR reaction tube is attached directly under sterile conditions and incubated for 1.5 min at 65° C. in an incubator or a heated closed system, with reaction vials placed upside down on the lid. Afterwards, the sample in the lid is briefly placed on ice, centrifuged for a short time, and again briefly incubated on ice.

Now, reverse transcriptase e.g. Superscript (SuperScript II Reverse Transcriptase RNase $H^-$ of the company Invitrogen 100 U/reaction) is added and the mixture is incubated at 37-38° C. for 2 h (Thermomixer Comfort Eppendorf; 38° C., Interval Mix). Preferably, 0.5 μl reverse transcriptase are used.

Subsequent to the lysis of cells and reverse transcription of RNA into cDNA, the detection and characterization of cDNA using expression analysis takes place. For this purpose, a qualitative PCR (e.g. Multiplex) is carried out directly. Alternatively, the mixture is immediately subjected to global PCR amplification, followed by microarray analysis. For quantitative gene expression analysis, a purification step for single-cell cDNA (Liss, Nuc Acids Research, 2002) is recommended.

As positive control, highly diluted midbrain-RNA or reference RNA (e.g. provided by Clontech or Ambion) is used which is treated in the same manner as the sample material.

The PCR provides the amplification of desired genes from isolated single cells, e.g. for a nested PCR. The PCR reaction is carried out under standard conditions, primers, buffer and incubation times are chosen in a way that they are suitable to amplify the desired genes in good quality.

One embodiment of the invention concerns a kit for the lysis of cells from a tissue specimen after microdissection and reverse transcription of RNA, containing at least a) lysis/cDNA-synthesis reaction buffer, filled under sterile conditions b) reverse transcriptase Based on the prevailing doctrine relating to the present invention and on the general expertise in this technical field, it is known to the manufacturer of this kit according to the present invention how to produce, formulate and store the single components of the kit, e.g. buffers, under sterile conditions.

If desired for the customer's service, the kit contains further materials for the dehydration of the tissue specimen such as 100% alcohol with molecular sieve and silica gel. In addition, a sterile reaction tube with a suitable lid for the uptake of cells after microdissection is added. Sterile in this context means that the reaction tube is RNase- and DNase-free.

It is claimed:

1. A method for a combined lysis and cDNA synthesis of RNA from a contamination-free single cell or cells of a tissue sample after laser microdissection, comprising the steps of:

(a) performing laser microdissection to prepare a single cell or cells from a tissue sample;

(b) transferring the microdissected single cell or cells contact-free to a sterile reaction tube with a lid by automatically laser pressure catapulting the micro dissected single cell or cells directly into the sterile reaction tube with a lid;

(c) adding a sterile lysis cDNA synthesis reaction buffer comprising DTT, Poly-I-Carrier RNA, Nonidet P40, dNTPs, random hexamer Primer and, an amount of an RNase inhibitor effective to provide the buffer RNase free to said sterile reaction tube with a lid and lysing the microdissected cells;

(d) following step (c), reverse transcribing RNA from the lysed cells in the same sterile lysis/cDNA synthesis reaction buffer in the same sterile reaction tube to produce cDNA; and (e) detecting the cDNA or detecting and characterizing the cDNA obtained according to step (d) by carrying out direct PCR without any further purification or other additional steps.

2. The method according to claim 1 wherein the single cells derive from a biological specimen.

3. The method according to claim 2 wherein the biological specimen is a tissue or an organ of a vertebrate.

4. The method according to claim 2 wherein the biological specimen is stained with a cresyl violet solution in alcohol.

5. The method according to claim 2 wherein the biological specimen is a dehydrated tissue section.

6. The method according to claim 5 wherein the dehydration is carried out in 100% ethanol with a molecular sieve.

7. The method according to claim 5 wherein the dehydrated tissue section is treated with a drying agent.

8. The method according to claim 7 wherein the drying agent is silica gel.

9. A kit for the combined lysis of cells from a tissue specimen after microdissection of a biological tissue specimen and reverse transcription of RNA to obtain cDNA from the biological tissue specimen, comprising:

a sterile lysis/cDNA-synthesis reaction buffer comprising:
10 mM DTT,
500 ng Poly-I-Carrier RNA,
an RNase inhibitor,
0.5% Nonidet P40,
0.5 mM dNTPs and
5 μM random hexamer Primer and reverse transcriptase.

10. The kit according to claim 9 further comprising a 100% ethanol solution with molecular sieve and silica gel.

11. A method for a combined lysis and cDNA synthesis of RNA from a contamination-free single cell or cells of a tissue sample after laser microdissection, comprising the steps of:

(a) performing laser microdissection to prepare a single cell or cells from a tissue sample;

(b) transferring the microdissected single cell or cells contact-free to a sterile reaction tube with a lid by automatically laser pressure catapulting the micro dissected single cell or cells directly into the sterile reaction tube with a lid;

(c) adding a sterile lysis cDNA synthesis reaction buffer comprising DTT, Poly-I-Carrier-RNA, Nonidet P40, dNTPs, random hexamer Primer and a protein based RNAse inhibitor of non-human origin, in an amount effective to provide the buffer RNase free, to said sterile reaction tube with a lid and lysing the microdissected cells;

(d) following step (c), reverse transcribing RNA from the lysed cells in the same sterile lysis/cDNA synthesis reaction buffer in the same sterile reaction tube to produce cDNA; and (e) detecting the cDNA or detecting and characterizing the cDNA obtained according to step (d) by carrying out direct PCR without any further purification or other additional steps.

12. A kit for the combined lysis of cells from a tissue specimen after microdissection of a biological tissue specimen and reverse transcription of RNA to obtain cDNA from the biological tissue specimen, comprising:

a sterile lysis/cDNA-synthesis reaction buffer comprising:
10 mM DTT,
500 ng Poly-I-Carrier RNA,
a protein based RNase inhibitor of non-human origin,
0.5% Nonidet P40,
0.5 mM dNTPs and
5 μM random hexamer Primer and reverse transcriptase.

13. The kit of claim 9 or 12, further comprising a sterile reaction tube with a lid.

* * * * *